United States Patent [19]

Suzuki et al.

[11] 4,251,195
[45] Feb. 17, 1981

[54] APPARATUS FOR MAKING MINIATURE CAPSULES

[75] Inventors: Toshiyuki Suzuki, Amagasaki; Kuniaki Matsumura, Ya'o; Hiroshi Maeda, Sakai; Akira Imai, Higashiosaka; Nobuo Kurokawa, Nara, all of Japan

[73] Assignee: Morishita Jinta Company, Limited, Japan

[21] Appl. No.: 962,043

[22] Filed: Nov. 20, 1978

Related U.S. Application Data

[63] Continuation of Ser. No. 749,755, Dec. 13, 1976, abandoned.

[30] Foreign Application Priority Data

Dec. 26, 1975 [JP] Japan ............................ 50/157935
Jun. 4, 1976 [JP] Japan ............................ 51/65308
Jun. 4, 1976 [JP] Japan ............................ 51/65309

[51] Int. Cl.³ .......................... B29F 3/10; B29C 23/00
[52] U.S. Cl. .................................... 425/6; 425/5; 425/70; 425/456; 264/7; 264/9
[58] Field of Search .................. 425/5, 6, 456, 804, 425/DIG. 101; 264/4, 7, 9; 425/70, 133.1

[56] References Cited

U.S. PATENT DOCUMENTS

| | | | |
|---|---|---|---|
| 2,379,816 | 7/1945 | Mabbs | 264/4 |
| 2,911,672 | 11/1959 | Van Erven Dorens et al. | 264/4 |
| 3,123,855 | 3/1964 | Fischer et al. | 425/6 |
| 3,397,258 | 8/1968 | Williams | 264/9 |
| 4,162,282 | 7/1979 | Fulwyler et al. | 264/9 |

Primary Examiner—James B. Lowe
Attorney, Agent, or Firm—Robert E. Burns; Emmanuel J. Lobato; Bruce L. Adams

[57] ABSTRACT

Apparatus for making miniature capsules having a capsule-forming orifice defined by the open ends of two coaxial conduits. The inner conduit defines a central opening in the orifice and the outer conduit defines an annulus circumferentially of the central opening. Filter-content material for the individual capsules is extruded as a stream through the central opening and a settable coating liquid material is extruded as a thin film sleeve circumferentially of the filler-content material stream. The film sleeve and the stream of filler-content material pass through a cooling liquid which is flowed through a fixed nozzle downstream of the extruding orifice. The nozzle has an inlet section with converging inner surfaces and a uniform diameter downstream of the inlet section. The cooling fluid, the film sleeve and filler-content stream therein all pass through the nozzle. A driven annular vibrator is disposed within the nozzle and develops vibrations in the cooling fluid parallel to the direction of the path of travel of the flow to form discrete droplets of the filler-content material enclosed in a film of the settable material. The droplets are recovered as miniature capsules.

4 Claims, 3 Drawing Figures

APPARATUS FOR MAKING MINIATURE CAPSULES

This is a continuation of application Ser. No. 749,755, filed Dec. 13, 1976, now abandoned.

BACKGROUND OF THE INVENTION

1. Field of the Invention

This invention relates to an apparatus for manufacturing seamless material-filled capsules, and miniature capsules having the values of particle diameter 0.5–4 mm, weight 1–30 mg, film percentage 5–30% and film thickness 0.05–0.2 mm.

2. Description of the Prior Art

According to a conventional apparatus for manufacturing seamless material-filled capsules, namely, in producing capsules of about 100 mg-500 mg by weight per capsule at a speed of manufacture, 4–10 capsules per second, the speed of manufacture has been found common to obtain 30 capsules per orifice per second as a maximum in the case of manufacturing small capsules of about 10 mg by weight per capsule.

Therefore, in manufacturing about 30 capsules per second by a conventional manufacturing apparatus, there occurs the problem of a capsule film material, capsule filler material as well as the influence of interfacial tension and restriction of manufacture due to much disturbance that the number of capsules per orifice has to be restricted and eventually both operation and apparatus are most apt to become complicated in many respects until the system of mass production of capsules is likely to be decreased in function. In fact, such tendency has become very large as particularly small capsules are to be manufactured.

In view of a conventional apparatus for manufacturing material-filled capsules and in order to improve the speed of manufacture in such a case, the applicant of the present application has carried out various tests and researches. As a result, the applicant has succeeded in exploiting an apparatus which is capable of manufacturing seamless material-filled capsules in the order of one figure larger than the maximal number of capsules to be manufactured per second by a conventional apparatus and at the same time, effecting the mass production of seamless material-filled capsules always of uniform capsule diameter and film thickness in a very rapid manner, regardless of the size of capsules.

Moreover, the seamless material-filled capsules thus obtained by the apparatus of the present invention can occur as miniature capsules, namely, in the form of much smaller capsules than capsules obtained by a conventional apparatus.

By employing the apparatus of the present invention, it is possible to improve the rate of manufacture of seamless material-filled capsules whereby mass production of capsules can be promoted to such an extent as has never been accomplished by a conventional apparatus. Indeed, as explained hereinbefore, it has become possible to attain the mass production of miniature capsules very easily, which has heretofore been considered difficult by a conventional apparatus, namely, miniature capsules of capsule diameter 0.5–4 mm, weight 1–30 mg, film percentage 5–30% and film thickness 0.05–0.2 mm.

Hitherto, capsules after formed as such have not been utilized satisfactorily to comply with their original object for use, because of various problems and unfavorable conditions such as the size of capsules and film thickness.

Now, material-filled capsules in the form of miniature capsules make according to the present invention can be used extensively in cases where, otherwise, the above mentioned bad results would usually prevail. Namely, by making material-filled capsules into miniature capsules, the extent of their utilization has become very wide and high in scope.

SUMMARY OF THE INVENTION

A first object of the present invention consists in providing an apparatus for manufacturing seamless double capsules consisting of a liquid capsule film material and a capsule-filler material using the open ended two concentric conduits as an orifice. The film material is set in a cooling liquid medium, wherein a ring body or vibrating body in the form of a cylinder is provided, just below, and a distance apart from, the lower end of the open ends of two coaxial conduits in the cooling liquid medium as to surround a jet stream of the capsule film material extruded from the orifice into the cooling liquid medium and to vibrate up and down with certain frequency along the lengthwise direction of the jet stream.

The second object of the present invention consists in providing an apparatus capable of manufacturing seamless material-filled capsules at the rate of one figure larger than the maximal number of capsules per second, which has been obtained by any apparatus of the prior art.

The third object of the present invention consists in considerably improving the mass production of capsules of prior art by largely increasing the speed of manufacture of seamless material-filled capsules.

The fourth object of the present invention consists in providing seamless material-filled capsules always of uniform capsule diameter and uniform film thickness, regardless of the size of the capsules.

The fifth object of the present invention consists in ensuring the mass production of miniature capsules having such values as capsule diameter 0.5–4 mm, weight 1–30 mg, film percentage 5–30% and film thickness 0.05–0.2 mm, which are much less than those of conventional capsules.

The sixth object of the present invention consists in obtaining the mass production of breath refresher and spice condiments in the form of miniature capsules as mentioned above.

BRIEF DESCRIPTION OF THE DRAWING

FIG. 2 is a view to show a vibrating body in the form of a ring. FIG. 3 is a view to show a vibrating body in the form of a cylinder.

DESCRIPTION OF THE PREFERRED EMBODIMENTS

Figure 1:
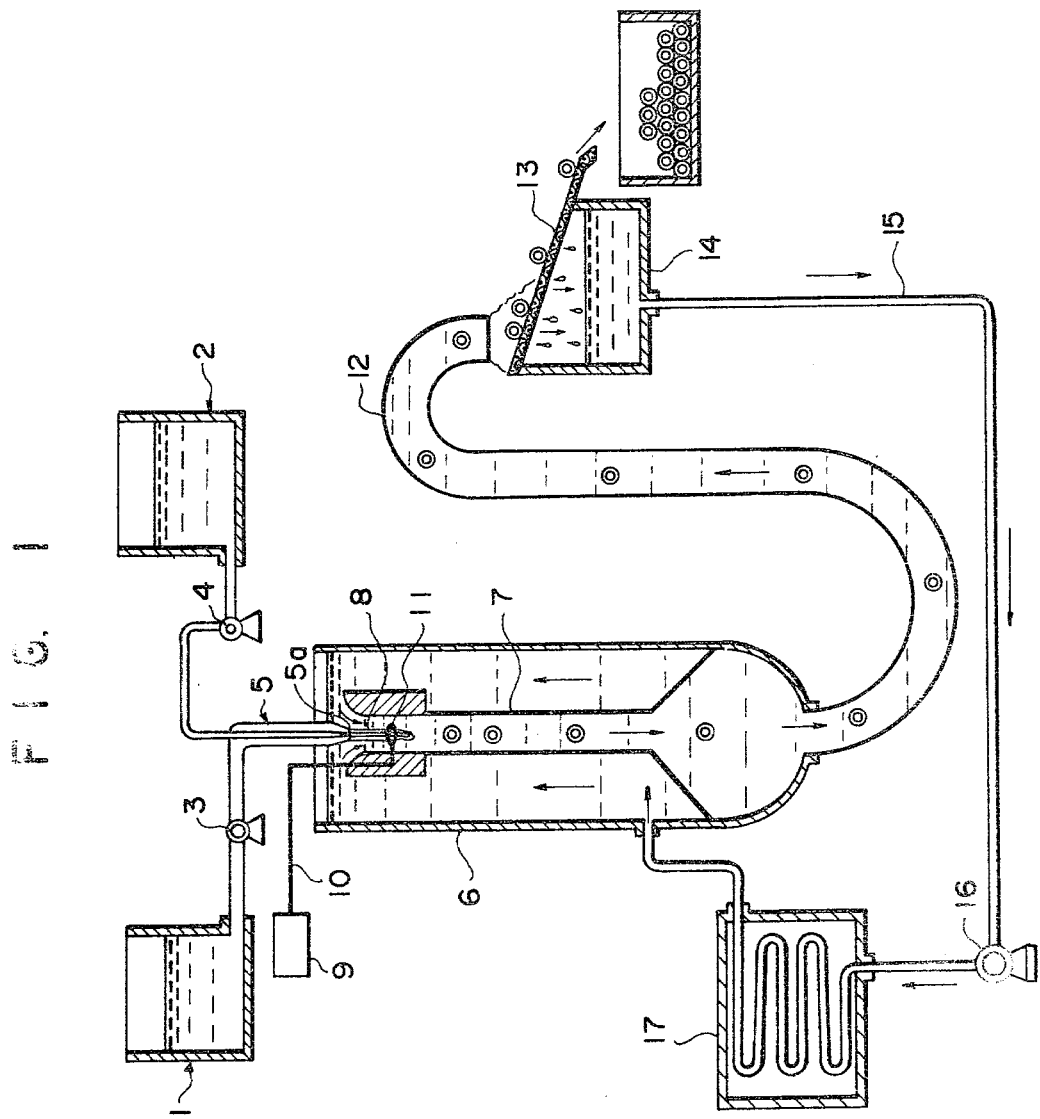
FIG. 1 is a general side elevation view of an apparatus for manufacturing seamless material-filled capsules, according to the present invention, which apparatus is capable of largely increasing the speed of manufacture of seamless material-filled capsules and obtaining seamless material-filled capsules in the form of miniature capsules.

The aforesaid objects and characteristics of the present invention will be understood accurately by way of the preferred embodiments with reference to the apparatus as shown in the accompanying drawings and their explanation in detail.

Firstly, the apparatus of the present invention will be explained with reference to FIG. 1.

Gelatin, D-sorbit, gum Arabic and water as a film material of capsule are stored in a tank 1. This tank 1 is connected to the outer cylindrical portion of a double cylindrical pipe 5 through a pump 3. Vegetable oil used as a capsule filler material is stored in a tank 2. This tank 2 is connected to the inner pipe of the coaxial conduits 5 through a pump 4. The lower end 5a of the conduits forms a capsule forming orifice opening downwardly in a capsule-forming cylinder 7 disposed in the main body 6 of a cooler and the capsule-forming cylinder has a uniform internal diameter at every point. Beneath the lower end or orifice 5a and a distance apart therefrom is provided a ring 11 or a cylinder 11a integral with a vibration-transmit lever 10 with a vibrator 9 so as to surround a jet stream 8 extruded from the double cylindrical orifice 5a into a cooling liquid medium in the lengthwise direction of jet stream 8. In connection with the extruded amount of the jet stream 8 is provided a recovery pipe 12 to promote the formation of capsules while cooling material-filled capsules continuously and beneath the discharge outlet of the capsule recovery pipe 12 is provided a net-like separator 13 for separating the finished capsules from the cooling liquid medium. Also beneath the separator 13 is provided a reservoir 14 of cooling liquid medium and the reservoir 14 is provided with a circulation pipe 15 for recovering the cooling liquid medium. The circulation pipe 15 is arranged in such a manner that the cooling liquid medium can be recycled to the main body 6 through a circulation pump 16 and a heat exchanger 17 for maintaining the temperature of the cooling liquid medium at a constant level.

With respect to the manufacture of seamless material-filled capsules at a quickened rate using the present apparatus, the present invention will be explained hereinafter.

A solution of capsule-film material composed of gelatin, D-sorbit, gum Arbic and water enters the outer cylindrical portion of the double coaxial conduits 5 of from the tank 1 through the pump 3. A capsule filler material composed of vegetable oil enters the inter cylindrical portion or conduit of the double pipe 5 from the tank 2 through the pump 4.

The aforesaid two solutions are extruded from the lower end 5a or double cylindrical orifice and are formed into the jet stream 8 at the orifice and flowed in a stream of cooling liquid medium and destined to descend in the capsule-forming cylinder 7. In this case, the flow speed of the cooling liquid medium in the capsule-forming cylinder 7 is adjusted to the most suitable speed which can be calculated from the diameter and number of capsules to be manufactured.

While the jet stream 8 remains as one of a uniform diameter, waves are caused or developed in the cooling liquid medium by means of the ring 11 vibrating up and down with a definite frequency due to the vibration of the vibrator 9. Upon receiving the influence of the waves of cooling liquid medium thus caused, the jet stream 8 too is made to develop waves.

While descending further, the jet stream 8 is squeezed and cut off drop by drop so as to become spherical capsule drops of uniform diameter due to interfacial tension.

Subsequently, the capsule drops thus formed keep descending in the capsule recovery pipe 12 and are cooled sufficiently and after the solution of capsule-film material has been solidified, the capsules and the cooling liquid medium are separated from each other by means of the separator so that the former can be obtained as seamless material-filled capsules here.

The cooling liquid medium thus separated through the separator 13 flows through a circulation pipe 15, and is fed into the heat exchanger through the pump 16, and after being cooled there, it will enter the capsule-forming cylinder 7 again for purposes of circulation. Owing to such circulation, it is possible to obtain seamless material-filled capsules of uniform diameter by mass production at a markedly increased speed.

Figure 2:
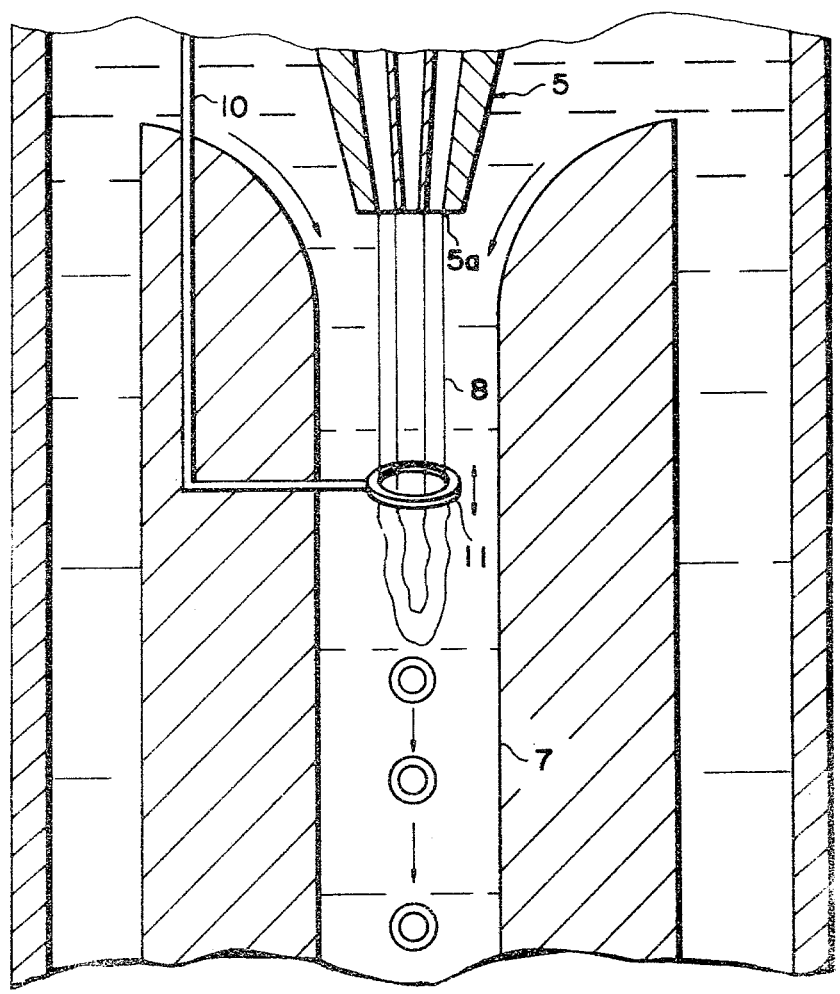
FIGS. 2 and 3 are cross-sectional views on an enlarged scale of parts of the present invention. Namely.

FIG. 2 is a view showing an enlarged view of environs of the orifice and vibrating ring of FIG. 1.

Figure 3:
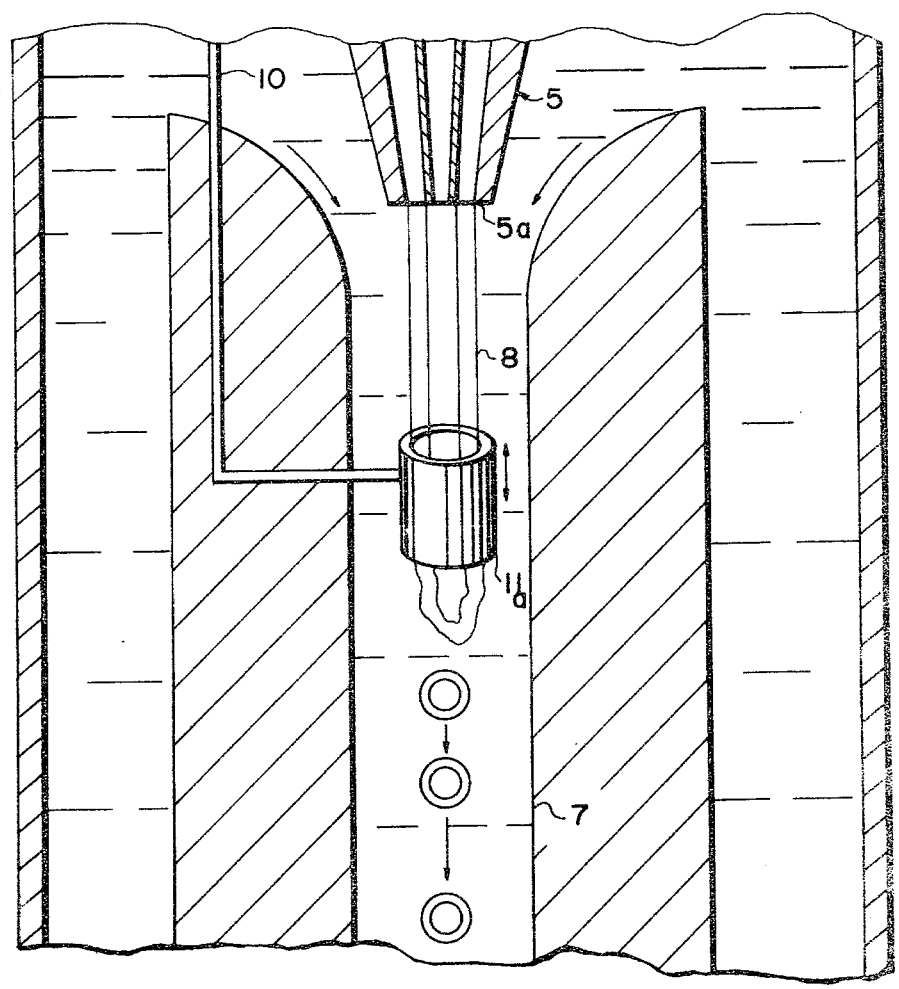

FIG. 3 is a view showing also an enlarged view of environs of the orifice and a thin-wall vibrating cylinder in place of a vibrating ring.

An explanation will be extended to miniature capsules which can be obtained by the apparatus of the present invention for manufacturing seamless material-filled capsules with the possibility of largely increasing the speed of manufacture. Namely, by so-called miniature capsules here are meant capsules of such values as those having a capsule diameter 0.5–5 mm, weight 1–30 mg, film percentage 5–30% and a film thickness of 0.05–0.2 mm.

The usual size of capsules of the prior art are of globular diameter, more than 4 mm, weight, more than 50 mg, film percentage, more than 30% and film thickness, more than 0.2 mm.

In comparing the values of both kinds of capsules, it is found that the difference between them is very considerable. Thus, the present invention has led to the possibility of mass production of miniature capsules in an easy and rapid manner, which fact should be called epoch-making in the industry of capsules for practical use.

Owing to the fact that it is possible to obtain miniature capsules by the apparatus of the present invention, an extremely high rate of utilization of such miniature capsules has been ensured, whereas capsules of such large size and film thickness of the prior art, even after being formed into so-called capsules, may nor correctly be called capsules. Now then, spice condiments in the form of miniature capsules will be explained.

For example, in the case of spice condiments for use as a sprinkle additive to instant food, the globular diameter of conventional capsules is so large, their form is so unfavourable and they are so heavy that the effect of spice in such capsules will be lost as unsuitable for use. On the other hand, the film of conventional capsules is so thick and slow in being dissolved that the effect of spice in them will be developed only very late thus leading to unfavorable results and almost losing the original value of their utilization in most cases.

When using a single condiment in the form of a capsule of the usual size, each globule becomes rather large. When attempting to enhance the concentration of such condiment, its taste will become too strong. Also in point of uniformity of taste, only one to three capsules for addition will be maximal so that they cannot be used satisfactorily after all because of the failure of uniformity of taste.

In contrast, in the case of preparing spice condiments in miniature capsules that can be obtained by the apparatus of the present invention for manufacturing material-filled capsules with the possibility of increasing the speed of manufacture. It is possible to obtain very large advantages, in points of carrying, preservation, cleanliness, handling, estimate of amount and accuracy for use. Moreover, the film of the miniature capsules is so thin that they can be dissolved very rapidly.

Here, two preferred embodiments of spice condiments in miniature capsules will be exemplified as follows.

PREFERRED EMBODIMENT 1

For use as spice for addition to instant noodle or cup noodle. Spice oil and sesame oil are mixed in the ratio of 7:3 to produce 14 mg of the resulting mixture by weight, which is enclosed in a film of 6 mg by weight of gelatin, D-sorbit and refined water to produce a miniature capsule.

PREFERRED EMBODIMENT 2

For use as liquid-like spice for addition to the aforesaid instant foods. Chinese oil, garlic oil and ginger oil are mixed in the ratios of 4:3:3 to obtain 14 mg of the resulting mixture by weight which is enclosed in a film of 6 mg by weight of gelatin, D-sorbit and refined water to produce a miniature capsule.

The method of manufacturing miniature capsules by the apparatus shown in FIG. 1 using the materials shown in the aforesaid preferred embodiments will be explained hereinbelow.

In FIG. 1, a solution composed of 15% gelatin, 5% glycerine and 80% water was stored in the tank 1, heated to 70° C. and fed to the coaxial conduits at the rate of 2 g per second by means of the pump. A solution of mixture of spice oil and sesame oil in the ratio of 7:3 was stored in the tank 2 and fed to the orifice 5a at the rate of 1.4 g per second by means of the pump 4. The vibrator 9 was vibrated at a frequency of 200 Hz and adjusted so that the ring 11 could be vibrated at the whole amplitude 0.5 mm. The ring 11 was disposed in a position about 30 mm below the lower end 5a of the orifice. The internal diameter of the capsule-firming cylinder 7 was 22 mm and a cooling liquid medium was adapted to cool vegetable oil to 0° C. and to flow at the rate of 80 cm on an average per second.

In this manner, it was possible to produce 200 seamless material-filled miniature capsules per second, each capsule of 10 mg by total weight containing 7 mg of spice oil and sesame oil.

Now, oral refrigerants or breath refreshers in the form of miniature capsules of the present invention will be explained hereinafter.

Since conventional capsules of oral refrigerants have too large a size and too thick a film, they are slow in being dissolved in the mouth and accordingly, their effect is developed slowly.

Even after being dissolved, the capsule feels foreign to the mouth and moreover, because of the capsule weighing as much as 100 mg, it is necessary to dilute peppermint oil with other oil so that the inherent refreshing feel of pepermint may be lost and the development of taste may cease until even an oil odor has occurred.

In contrast, when preparing a breath refresher in miniature capsules obtained by the apparatus of the present invention, the above-mentioned disadvantages can be completely eliminated. Namely, in such a case, by dint of the thin film of each miniature capsule, the capsule will be dissolved rapidly in the mouth and never feels foreign to the mouth. At the same time, since peppermint oil only as an oral refresher can be enclosed in a miniature capsule of 10 mg by weight, the fragrance and taste of its contents are found very good and such miniature capsules are easy to carry and handle with good preservative properties. Two preferred embodiments of breath refreshers in miniature capsules will be explained hereinbelow.

PREFERRED EMBODIMENT 1

Peppermint oil was enclosed in a film composed of D-sorbit and refined water to result in a capsule of 10 mg by weight consisting of 8 mg as contents of peppermint oil and 2 mg of film.

PREFERRED EMBODIMENT 2

A miniature capsule was introduced as a single-nuclear double capsule. It was 30 mg heavy enclosing a mixture of orange oil, granule sugar and edible oil in the ratios of 35:30:35, the contents weighing 21 mg and being enclosed in an intermediate layer of 4.5 mg by weight in the form of a mixture of gelatin, refined vegetable oil, D-sorbit and refined water in the ratios of 10:30:2:58 and then the intermediate layer was enclosed in an outer layer of 4.5 mg by weight in the form of a mixture of gelatin, D-sorbit and refined water in the ratios of 20:10:70 so that the resulting capsule occurred in the form of the above mentioned single-nuclear double capsule.

A single-layer miniature capsule in cases of a breath refresher can be obtained by the same method and apparatus as those of spice condiments. Lastly, all effects obtained by the method and apparatus of the present invention will be explained hereinafter.

(1) By dint of the apparatus of the present invention, it is possible to quicken the speed of manufacture of seamless material-filled capsules to a large extent and to ensure the mass production of seamless material-filled capsules as high as one figure larger than the maximal number of capsules per second which have been heretofore obtained by conventional methods and apparatus. Thus, this excellent effect has led to improving the system of mass production of capsules which has never been attained by conventional apparatus.

(2) Regardless of the size of capsules, it is possible to always obtain seamless material-filled capsules of uniform diameter and film thickness.

(3) It is possible to obtain such an effect as the mass production of miniature capsules of diameter 0.5–4 mm, weight 1–30 mg, film percentage 5–30% and film thickness 0.05–0.2 mm. This outstanding effect has led to the extensive use of miniature capsules in cases where capsules of conventional film thickness fail to develop by market and to answer to their original requirements for use. Thus, miniature capsules of the present invention for use in the fields of condiments, breath refreshers medicines, foods, luxuries and bath agents will be highly appreciated and their practical value will prove very significant.

What is claimed is:

1. Apparatus for making miniature capsules comprising, means defining a capsule-forming orifice comprising, two coaxial conduits terminating as two concentric open ends defining a central opening and an annulus circumferentially of the central opening, means for delivering filler-contents of a capsule to the inner conduit of said two coaxial conduits extruded therefrom through said central opening as a stream, means delivering a settable coating liquid material to an outer one of said conduits for forming a capsule and extruded from said annulus as a stream defining an extruded film sleeve circumferentially of said stream for coating droplets of said filler-contents, means for delivering a cooling stream of cooling liquid along a path of travel parallel to and circumferentially of said stream of filler-contents and said film sleeve of settable coating material, means defining in said path, a fixed nozzle in said path adjacent said central opening and annulus and through which said cooling stream is developed as a flow circumferential of said filler-contents stream and film sleeve and through which all of said filler-contents stream and film sleeve pass, said nozzle having a converging inlet section and a constant inner diameter downstream of said inlet section, a driven annular vibrator internally of said nozzle and through which said filler-contents stream and film sleeve pass and are subjected to vibrations developed in said cooling stream parallel to said path of travel to develop discrete droplets of said filler-contents enclosed within said settable coating material, and means to recover the droplets as capsules along said path of travel.

2. Apparatus for making miniature capsules according to claim 1, said means to recover said droplets as capsules including means for draining off said cooling liquid therefrom, and means to return cooling liquid drained off said capsules to said means defining said path.

3. Apparatus according to claim 1, in which said vibrator is a ring.

4. Apparatus according to claim 1, in which said vibrator is a cylinder.

* * * * *